(12) United States Patent
Fischer et al.

(10) Patent No.: US 12,357,768 B2
(45) Date of Patent: Jul. 15, 2025

(54) PROTECTIVE DEVICE FOR A SYRINGE NEEDLE TUBE

(71) Applicant: SAFEJECT INTERNATIONAL PTE LTD, Singapore (SG)

(72) Inventors: Stephan Fischer, Hiddenhausen (DE); Tobias Wilke, Ibbenbueren (DE); Bernd Mohr, Barnstedt (DE)

(73) Assignee: Safeject International Pte Ltd, Singapore (SG)

( * ) Notice: Subject to any disclaimer, the term of this patent is extended or adjusted under 35 U.S.C. 154(b) by 0 days.

(21) Appl. No.: 18/935,754

(22) Filed: Nov. 4, 2024

(65) Prior Publication Data

US 2025/0135123 A1 May 1, 2025

Related U.S. Application Data

(63) Continuation of application No. PCT/EP2023/061677, filed on May 3, 2023.

(30) Foreign Application Priority Data

May 5, 2022 (DE) .......................... 102022111083.4

(51) Int. Cl.
  *A61M 5/32* (2006.01)
(52) U.S. Cl.
  CPC ................. *A61M 5/3202* (2013.01)
(58) Field of Classification Search
  CPC .............. A61M 5/3202; A61M 5/3213; A61M 5/3243; A61M 5/3216
  See application file for complete search history.

(56) References Cited

U.S. PATENT DOCUMENTS

| | | |
|---|---|---|
| 5,490,841 A | 2/1996 | Landis |
| 2004/0078007 A1* | 4/2004 | Nguyen ............... A61M 5/3216 128/919 |
| 2008/0208138 A1* | 8/2008 | Lim ..................... A61M 5/3216 604/192 |
| 2009/0018510 A1* | 1/2009 | Madin ................. A61M 5/3216 604/192 |
| 2010/0198152 A1* | 8/2010 | Haindl ................ A61M 5/3216 604/110 |

(Continued)

FOREIGN PATENT DOCUMENTS

| | | |
|---|---|---|
| DE | 102017120538 A1 | 3/2019 |
| DE | 202019103876 U1 | 7/2019 |
| WO | WO2021008717 A1 | 1/2021 |

*Primary Examiner* — Dung T Ulsh
(74) *Attorney, Agent, or Firm* — Von Rohrscheidt Patents (57) ABSTRACT

A protective device for a needle tube of a syringe, the protective device including a base; and a cover connected to the base, wherein the base s configured to cooperate with a needle carrier by positive form locking wherein the needle carrier supports the needle tube, wherein the cover is configured elongated along a longitudinal axis and defines an interior space in which the needle tube is storable so that a person is protected against an unintentional contact with the needle tube, wherein the cover is pivotably supported at the base so that the cover is transferable relative to the base within a pivot plane from a starting position where the needle tube is stored in the interior before being used for injection in a first pivot direction into an operating position where the needle tube is available for injection.

13 Claims, 8 Drawing Sheets

(56) References Cited

U.S. PATENT DOCUMENTS

2014/0221872 A1\* 8/2014 Lin ................. A61B 5/150519
  600/576
2020/0078532 A1  3/2020 Madin \* cited by examiner

PROTECTIVE DEVICE FOR A SYRINGE NEEDLE TUBE

RELATED APPLICATIONS

This application is a continuation of international patent application PCT/EP2023/06177 filed on May 3, 2023 claiming priority from German patent application DE 10 2022 111 083.4 filed on May 5, 2022, both of which are incorporated in their entirety by this reference.

FIELD OF THE INVENTION

The instant invention relates to a protective device for a needle tube of a syringe. The invention furthermore relates to a set including a protective device and a needle carrier with a needle tube supported therein.

BACKGROUND OF THE INVENTION

A generic protective device is already known from WO 2021/008717 A1. This document describes a protective device including a cover including a retaining device configured to reliably retain the needle tube. The retaining device includes two lobes which extend towards each other respectively originating from an inner developing surface of a wall of the cover. Thus, the lobes are inclined relative to the pivot plane and elastic so that the needle tube can deform and displace the lobes and thus interlock behind the lobes. This way it is assured that the needle tube cannot exit from the safety area defined behind the lobes when pivoting the cover relative to the base of the protective device so that an unintentional injury of a person through the needle tube is prevented.

Though safety of the known protective device against unintentional exit of the needle tube from the safety area is substantial already, intentional mishandling of the safety device is still possible and might cause the needle tube to exit the safety area after being used for the injection which poses a risk of a subsequent infection.

U.S. Pat. No. 5,490,841 B1 discloses another protective device with a cover. The cover includes a retaining device which includes a lobe that is oriented at a slant angle within an interior of the cover. The cover encloses a needle tube after use reliably in a safety area of the interior of the cover wherein the lobe is configured flexible so that it is initially elastically deformable in order to let the needle tube enter the safety area. A deformation in the opposite direction that leads to an exit of the needle tube from the safety area is prevented by a stop that is configured at an inner developing surface of the wall of the cover at a location that is arranged opposite to the lobe.

This configuration is disadvantageous since the lobe extends within the interior of the cover so that the lobe can collide with the needle tube before being used for the injection. This is disadvantageous in particular with respect to automated production of the syringe which is configured with a needle carrier including a needle tube and a protective device since the protective device cannot be easily mounted with its base on or at the needle carrier without causing a collision of the needle tube supported in the needle carrier with the lobe arranged in the interior of the cover.

BRIEF SUMMARY OF THE INVENTION

Thus, it is an object of the invention to provide a protective device that is applicable to a needle carrier in a particularly simple manner and which also provides a high level of safety against an unintentional exit of the needle tube from the cover after being used for the injection.

The protective device includes a base and a cover connected with the base. The cover is pivotable relative to the base, wherein the base and the cover are typically connected with one another by a film hinge. The base is configured to cooperate with a needle carrier by positive form locking. The needle carrier is configured to support the needle tube. Thus, the needle tube is typically centrally glued into a recess of the needle carrier, so that a force-transmitting connection is provided between the needle tube and the needle carrier. Due to the form-locking connection of the base with the needle carrier, the base is typically fixed at the needle carrier.

The cover is elongated and extends along a longitudinal axis. The cover defines an interior space in which the needle tube is supportable so that a person is protected against unintentional contact with the needle tube. Persons in particular should be protected against unintentional contact with a needle tip of the needle tube, in particular after a needle tube has been used for an injection. This this way it can be prevented that infectious diseases are transferred from a patient that was injected with the needle tube to a person treating the patient.

Pivotability of the cover relative to the base is provided so that the cover is movable in a pivot plane relative to the base. This way the cover can be transferred relative to the base in a first pivot direction from a starting position where the needle tube is supported in an interior of the cover before being used for injection into an operating position. In the operating position the needle tube is available for injection, this means the needle tube is not in the interior of the cover anymore. After being used for injection, the cover is transferrable from the operating position in a second pivot direction that is opposite to the first pivot direction into a protective position where the needle tube is supported in the interior again after being used for the injection. Thus, the needle tube is protected against unintentional contact with a person in the manner described supra.

In order for the needle tube to be able to exit from the cover when the cover transitions from the starting position into the operating position and eventually enter into the cover again when the cover returns from the operating position into the protective position, the cover is open on one side in the pivot plane. In particular, a wall of the cover that envelops the interior of the cover may envelop the interior at three sides only while the fourth side is open.

The cover includes a retaining device in an interior of the cover, the retaining device configured to interlock the needle tube by positive form locking while transferring the needle tube into the protected position. This interlocking is done so that an unintentional exit of the needle tube from the interior space is prevented after the cover is transferred into the protective position. Put differently, the retaining device is used to retain the needle tube so that a renewed pivoting of the cover relative to the base after using the needle tube for injection does not cause the needle tube to be released.

The object is achieved by a protective device for a needle tube of a syringe, the protective device including a base; and a cover connected to the base, wherein the base s configured to cooperate with a needle carrier by positive form locking wherein the needle carrier supports the needle tube, wherein the cover is configured elongated along a longitudinal axis and defines an interior space in which the needle tube is storable so that a person is protected against an unintentional contact with the needle tube, wherein the cover is pivotably supported at the base so that the cover is transferable relative to the base within a pivot plane from a starting position where the needle tube is stored in the interior before being used for injection in a first pivot direction into an operating position where the needle tube is available for injection, and eventually transferrable in a second pivot direction opposite to the first pivot direction into a protective position where the needle tube is stored in the interior space again after being used for injection, wherein the cover is open at one side in the pivot plane so that the needle tube is able to initially exit from the interior space for injection by performing the pivot movement of the cover in the first pivot direction and able to enter the interior space again by performing the pivot movement of the cover in the second pivot direction after being used for the injection, wherein the cover includes a retaining device in the interior space wherein the retaining device is configured to interlock the needle tube by positive form locking during a transfer of the cover into the protective position so that an unintentional exit of the needle tube from the interior space is prevented after a completion of the transfer of the cover into the protective position, wherein the retaining device includes a deformable lobe, a stop associated with deformable the lobe and at least one guide element, wherein the deformable lobe is configured to be deformed by the needle tube during transfer of the cover into its protective position and displaced in a first displacement direction so that the needle tube is able to enter into a safety area arranged behind the deformable lobe deformable in which the needle tube is interlocked behind the deformable lobe, wherein the stop is configured at the inner enveloping surface of the cover opposite from the deformable lobe, so that the deformable lobe when deformed by the needle tube contacts a contact surface of the stop in a second displacement direction opposite to the first displacement direction so that an unintentional exit of the needle tube from the safety area is prevented, wherein the guide element is associated with the stop and configured to guide the needle tube so that a presence of the needle tube below a stop surface of the stop is prevented after the needle tube enters the safety area, wherein the deformable lobe extends in undeformed condition from the inner enveloping surface of the cover into the interior space and defines a lobe angle of at least 35° with the pivot plane viewed in a cross section orthogonal to the longitudinal axis of the cover.

Advantageous embodiments can be derived from the dependent claims.

The protective device according to the invention is characterized in that the retaining device includes a deformable lobe, a stop associated with the lobe and at least one support element. The lobe is configured to be deformed by the needle tube while transferring the cover into its protective position so that the lobe is displaced in a first direction, so that the needle tube can enter a safety area of the interior that is arranged behind the lobe. This way the needle tube is interlocked behind the lobe so that the lobe retains the needle tube in the safety area and thus prevents an unintentional release of the needle tube. The stop is formed opposite to the lobe at an inner enveloping surface of the cover or its wall and configured so that the lobe when deformed by the needle tube in a second direction oriented against the first direction contacts a lower contact surface of the stop so that a further deformation of the lobe is prevented. This prevents an unintentional exit of the needle tube from the from the safety area.

In an undeformed condition the lobe extends from the inner enveloping surface of the cover into the interior of the cover, wherein the lobe encloses a lobe angle of at least 35° with the pivot plane in an advantageous embodiment in a cross section that runs orthogonal to the longitudinal axis of the cover. Advantageously this angle is at least 40°, further advantageously 45°.

The at least one guide element is associated with the stop and configured to guide the needle tube arranged in the safety area so that a presence of the needle tube below the contact surface of the stop is prevented after the needle tube enters the safety area. In particular, the guide element can block a space below the stop so that the needle tube contacts the guide element laterally and thus cannot move into the space below the stop. This way it can be prevented that the needle tube moves below the stop and then between the lobe and the stop after having entered the safety area, so that the needle tube would exit the safety area again.

The safety device according to the invention has many advantages. In particular the protective device assures safe keeping of the needle tube within the cover after the needle tube has been used for an injection and the cover has been pivoted into its protective position. The reason is that the needle tube cannot exit from the safety area anymore after the needle tube has entered into the safety area since entering the safety area requires a temporary displacement of the elastic lobe. A movement of the needle tube in a direction out of the safety area inevitably causes the needle tube to contact the lobe from a bottom side which elastically deforms the lobe again but, this deformation causes the lobe to contact the contact surface of the stop due to the adapted geometry of the lobe and the stop which prevents a further deformation of the lobe. The at least one guide element assures that the needle tube contacts the bottom side of the lobe and in particular cannot contact a stop side of the stop directly laterally from the lobe. Tests have shown that it is not possible to remove the needle tube from the safety area after entry therein even when the protective device is intentionally tampered with.

Thus, it is another advantage of the invention that the protective device can be mounted on a needle carrier that is configured with a needle tube easily. Thus, a collision of the needle tube with the lobe of the cover is prevented when the cover is in its starting position. This is achieved by a slope of the lobe that is rather steep with reference to the pivot plane and which is at least 35° according to the preceding description. Known covers are inclined relative to the pivot plane at a significantly flatter angle and extend essentially centrally through the interior of the cover. However, when the cover is in its starting position the needle tube fills this area so that a collision of the needle tube with this flatter lobe would most likely occur during mounting of the cover.

It is another advantage of the configuration according to the invention that the safety against the exit of the needle tube from the safety area is provided by the cooperation of the soft lobe with the rigid stop. This facilitates that the lobe itself can be configured comparatively soft, this means with little stiffness since the lobe does not secure the needle tube by itself. Thus, a slight deformability of the lobe does not impair the safety, since the lobe can be deformed easily when the needle tube contacts the bottom side of the lobe, but a movement of the lobe into the opposite direction is prevented due to the contact of the lobe at the contact surface of the stop. The easy deformability of the lobe, however, has the particular advantage that the protective device is also useable when a thin needle tube it used. In particular needle tubes that are used e.g., for insulin syringes have a particularly small diameter so that the needle tube is deformable particularly easily. When the lobe is configured stiff like in the prior art in order to secure the needle tube in the safety area, the needle tube may not be able to displace the lobe, but the lobe would deform the needle tube. This would prevent a reliable entry of the needle tube into the safety area which renders the syringe with this protective device unsafe. This lack of safety would not be caused by the fact that the needle tube can exit the safety area unintentionally, but by the fact that the needle tube cannot enter the safety area reliably. The soft lobe eliminates this risk.

In an advantageous embodiment of the protective device according to the invention, a cross section of the cover orthogonal to the longitudinal axis of the cover shows an offset between an end of the non-deformed lobe oriented away from the inner enveloping surface of the cover and an end of the stop oriented towards the cover wherein the offset is measured in a direction orthogonal to the pivot plane. Put differently an offset measured orthogonal to the pivot plane is provided in this embodiment between ends of the stop and the lobe oriented towards each other. This offset is advantageously in a range between 0.05 mm and 0.25 mm, further advantageously between 0.1 mm and 0.2 mm. Thus, the undeformed lobe does not reach under the contact surface of the stop in this embodiment. Instead, a minimum gap is provided between the lobe and the stop which facilitates an entry of the needle tube into the safety area in the interior of the cover. In particular only a small deformation of the lobe is required so that the needle tube can enter the safety area and snap behind the lobe. Accordingly, this configuration is particularly advantageous to facilitate an entry of the needle tube into the safety area with little force impact upon the needle tube so that the entry can be provided particularly reliably and an unintentional deformation of the needle tube is prevented.

Additionally, an embodiment of the protective device is particularly advantageous where a cross section of the cover orthogonal to the longitudinal axis of the cover shows an offset between an end of the undeformed lobe that is oriented away from the inner enveloping surface of the cover and an end of the stop oriented towards the lobe wherein the offset is measured in a direction parallel to the pivot plane. The offset is advantageously in a range between 0.20 mm and 0.80 mm, further advantageously between 0.20 mm and 0.70 mm, further advantageously between 0.30 mm and 0.60 mm. This embodiment also has the advantage that the entry of a needle tube into the safety area is simplified since the lobe only has to be displaced by a minimum amount in order for the needle tube to snap lock behind the lobe. As a matter of principle, the needle tube can pass through a slot between the lobe and the stop formed due to the offset described supra and exit the safety area this way. This however is prevented by the guide element which guides the needle tube so that it cannot move under the stop and thus, cannot access the provided slot. Thus, a movement of the needle tube in a direction out of the safety area causes the needle tube to contact the bottom side of the lobe, which causes the deformation of the lobe described supra until the lobe contacts the contact surface of the stop.

Advantageously, the at least one guide element extends from the inner enveloping surface of the cover into the into the interior. This advantageously is performed so that the space below the contact surface of the cover is blocked completely for the needle tube. The associated advantages are described supra.

It is particularly advantageous when the protective device includes a plurality of guide elements wherein at least one guide element is arranged in front of the stop and at least one guide element is arranged behind the stop viewed in the longitudinal direction of the cover. This configuration has the advantage that a movement of the needle tube into the space below the contact surface of the cover is prevented reliably when the needle tube is deformed, in particular bent along its longitudinal axis. Thus, the space below the contact surface of the cover is blocked from both sides of the cover by the two support elements so that the needle tube cannot reach this space and is thus reliably retained under the lobe.

In another embodiment of the protective device according to the invention, the cover has a U-shaped wall in a cross section orthogonal to the longitudinal axis of the cover wherein the wall defines the interior space. Thus, the cover is advantageously configured so that a vertical axis of a cross-section of the cover is oriented parallel to the pivot axis of the cover. In particular, a cross-section of the cover can be at least essentially parallel at opposite inner enveloping surfaces from which the lobe extends on one side and the stop extends at the other side. A corresponding configuration can be derived from the subsequent embodiment. This configuration is particularly advantageous in order to secure the cooperation of the lobe and the stop.

Advantageously, the protective device is configured so that the base and the cover are connected with one another in their starting position by a rated fracture joint ("originality closure") in a force transferring manner. The rated fracture joint can be broken by applying a hand force so that the cover is pivotable into its operating position after the rated fracture joint is broken. This embodiment is particularly advantageous in order to reliably support the needle tube within the cover before being used for injection wherein the rated fracture joint prevents an unintentional pivoting of the cover into the operating position and thus an unintentional release of the needle tube. Furthermore, it is not required for the protection of the needle tube to use a separate cover before using the needle tube for injection wherein the separate cover would be placed over the needle tube e.g., in a form of a closed cap. Instead, the function of protecting the needle tube before being used for injection and also after being used for injection can be performed by the cover itself. This is particularly easy due to the configuration described supra of the lobe that is inclined at a steep angle relative to the pivot plane since the described risk of a collision of the needle tube with the lobe is eliminated during assembly of the protective device at the needle carrier. When the rated fracture joint is destroyed it becomes an indicator that the needle tube may already have been used. Thus, a user of the protective device would not use a needle tube anymore when he or she has not opened the protective device himself or herself, this means he or she has destroyed the rated fracture joint.

In another advantageous embodiment of the protective device according to the invention, the cover and the base are connected with one another by a foil hinge. The foil hinge is particularly well suited to establish the pivotability of the cover relative to the base while simultaneously providing an integral configuration of the protective device in one piece. Thus, it is particularly advantageous when the protective device is integrally provided in one piece.

Furthermore, a configuration of the protective device can be effectively advantageous where the cover and the base are arranged coaxial relative to each other when the cover is in its starting position. In this embodiment the longitudinal axis of the base and the cover are oriented parallel to each other. Advantageously the longitudinal axis of the cover and the base coincide.

Alternatively, or additionally is can being particularly advantageous when the cover is pivoted in the second pivot direction when the cover is in its protective position so that the longitudinal axis of the base and the cover are not oriented parallel to one another, thus enclose an angle greater and 0° relative to each other. This configuration has the advantage that the needle tube can be brought in contact with the lobe in a particularly simple manner which displaces the lobe as described supra so that the needle tube eventually enters the safety area in the interior of the cover. In an embodiment where the cover is inclined at different angles relative to the base between its starting position and its protective position, it is particularly simple to prevent a collision of the needle tube with the cover when mounting the protective device at a needle carrier, however this collision is intentionally caused when transferring the cover into the protective position in order to let the needle tube enter into the safety area. Furthermore, the described embodiment is advantageous in that the cover can be attached at the base in a particularly simple manner in order to secure the cover in its protective position, advantageously by using positive form locking.

Accordingly, it can be particularly advantageous when at least one interlocking device is configured at the base wherein the interlocking device cooperates with at least one interlocking partner of the cover by positive form locking so that the cover is interlockable in the protective position. The cooperation of the interlocking device with the interlocking partner can be implemented in a particularly simple manner by pivoting the cover beyond the starting position relative to the base when transferring the cover into the protective position, so that the interlocking partner of the cover is brought in contact with the interlocking device of the base. Due to the engagement of the interlocking partner with the interlocking device it is assured that the cover is not moved from its protective position back into its operating position unintentionally.

The object is also achieved by a set with the features of claim 12. An advantageous embodiment can be derived from the associated dependent claim.

The set includes a protective device according to the invention as described supra and a needle carrier with a needle tube supported therein. The base of the protective device is connected with the needle carrier by positive form locking so that the needle tube is oriented parallel to a longitudinal axis of the cover when the cover is in its starting position. When the cover is pivoted from its starting position into its operating position in a first pivot direction in the pivot plane, the needle tube is released for injection use. Subsequently the cover can be pivoted in a second pivot direction that is opposite to the first pivot direction back in a direction towards the starting position so that the needle tube enters into the interior of the cover again and is protected against an unintentional contact with a person. As recited supra it is particularly advantageous when the cover is locked relative to the base when the cover reaches its protective position, so that moving the cover into the operating position again is prevented. Moving the cover into the protective position coincides with an entry of the needle tube into the safety area beyond the lobe, wherein the lobe is elastically deformed due to a contact with the needle tube and thus displaced until the needle tube snaps in place behind the lobe and is disposed in the safety area thereafter.

In a particularly advantageous embodiment of the set according to the invention, a lobe base of the lobe viewed in a cross section of the cover orthogonal to the longitudinal axis of the cover is arranged in a common plane with the needle tube that is perpendicular to the pivot plane at least when the cover is in its starting position. Thus, the lobe base designates a proximal portion of the lobe by which the lobe is connected to an inner enveloping surface of the wall of the cover. The described embodiment has the advantage that a collision of the lobe with the needle tube is prevented during mounting of the protective device at the needle carrier since the needle tube and the lobe base are at an identical elevation level with respect to the pivot plane of the cover. Since the lobe extends at an angle relative to the pivot plane and the needle tube typically runs through a center of the interior space of the cover, the lobe extends as a consequence past the needle tube in a direction towards the pivot plane. This embodiment will be described infra.

BRIEF DESCRIPTION OF THE DRAWINGS

The invention is now described based on an embodiment with reference to drawing figures, wherein.

DETAILED DESCRIPTION

The embodiment illustrated in FIGS. 1-8 includes a protective device 1 including a base 3 and a cover 4. The cover 4 is configured pivotable relative to the base 3 wherein the cover 4 is connected by a foil hinge 22 at the base 3. The protective device 1 is configured integrally in one piece and produced as an injection molded part.

The base 3 is configured to cooperate with a needle carrier 25 that supports a needle tube 2. The needle tube 2 is glued in particular into a complementary recess of the needle carrier 25 so that a longitudinal axis of the elongated needle tube 2 runs parallel to a longitudinal axis 31 of the base 3. This is evident in particular from FIG. 1.

The protective device 1 is mounted in its entirety at the needle carrier 25 which is advantageously performed automatically. During assembly the protective device 1 is in a starting position where the cover 4 is in a starting position. In this starting position the cover 4 is attached at the base 3 by a rated fracted joint 21, so that a pivoting of the cover 4 relative to the base 3 is blocked. When the cover 4 is in its starting position, a longitudinal axis 5 of the cover 4 and the longitudinal axis 31 of the base 3 are oriented parallel to one another. In the illustrated embodiment, the cover 4 is configured coaxial to the base 3 so that the longitudinal axes 5, 31 of the cover 4 and of the base 3 coincide.

After mounting the protective device 1 on the needle carrier 25, the needle tube 2 is arranged within an interior space 6 of the cover 4 that is enveloped by a wall 30 of the cover 4. This is evident in particular from FIG. 2. Supporting the needle tube 2 within the cover 4 has the advantage that a person handling the syringe that includes the needle carrier 25, is protected against injury from a needle tip 35 of the needle tube 2. The blocking of the pivot movement of the cover 4 relative to the base 3 by the rated fracture joint 21 prevents an unintentional release of the needle tube 2.

In order to render the needle tube 2 usable for injection, it is necessary to release the needle tube 2. Thus, the user of the syringe can break the cover 4 from the base 3 by applying a hand force at a grip lobe 33 of the cover 4 so that the rated fracture joint 21 is destroyed. This releases the pivotability of the cover 4 relative to the base 3 using the foil hinge 22. Accordingly, the cover 4 can be moved into its operating position by pivoting the cover 4 in a first pivot direction within the pivot plane 8, so that the needle tube 2 is released into the operating position. Thus, the cover 4 is pivotable within the pivot plane 8 relative to the base 3, wherein a wall 30 of the cover 4 is open in the pivot plane 8 at one side so that the needle tube 2 can exit from the interior space 6 easily during the pivoting of the cover 4. This is clearly evident from FIG. 2. In the illustrated embodiment the wall 30 is configured U-shaped, wherein a vertical axis 20 of a cross section of the wall 30 is oriented parallel to the pivot axis 8 and orthogonal to the longitudinal axis 5 of the cover 4.

Figure 5:
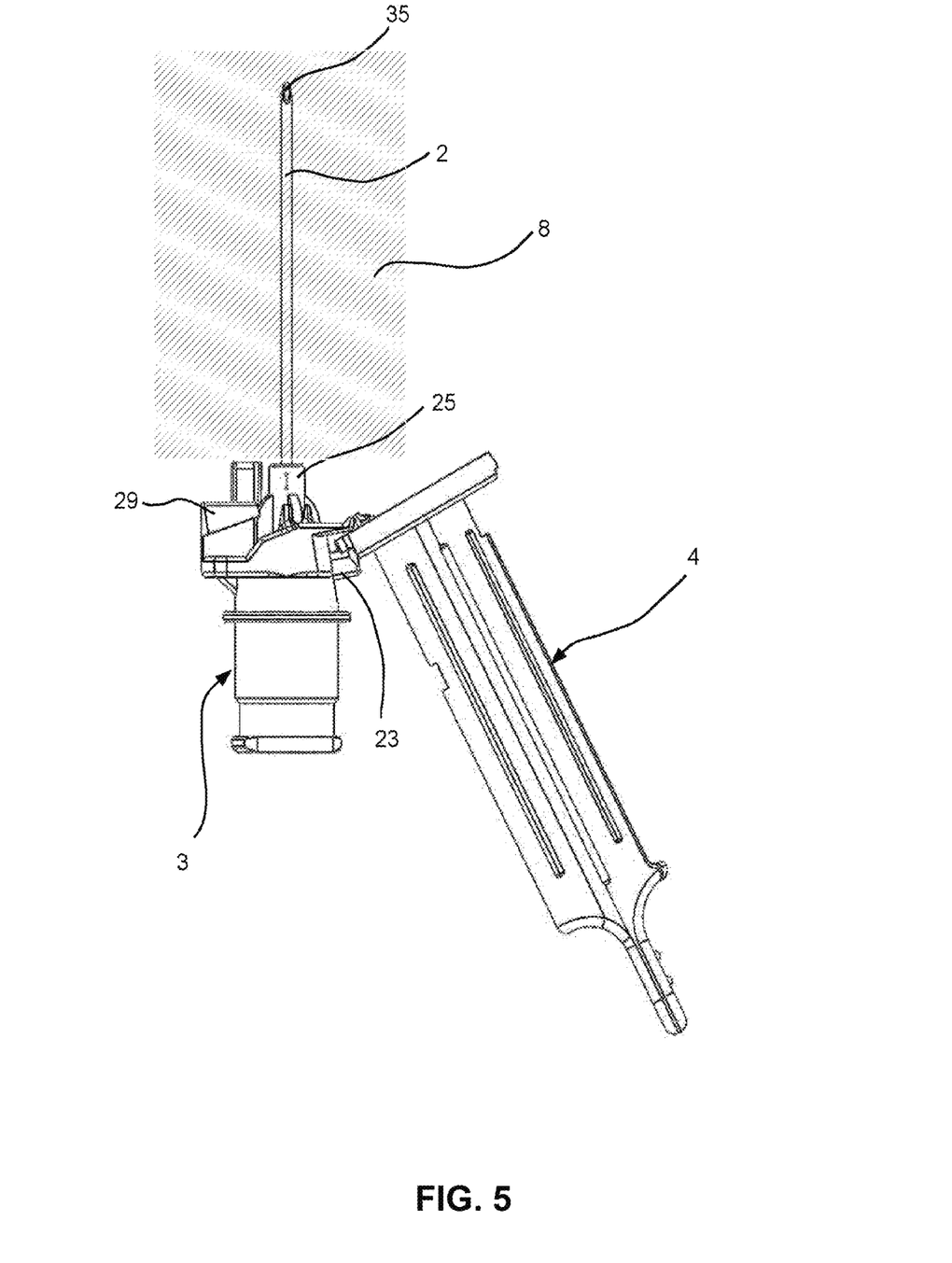
FIG. 5 illustrates a view of the protective device according to FIG. 1 with the cover in the operating position.
Figure 6:
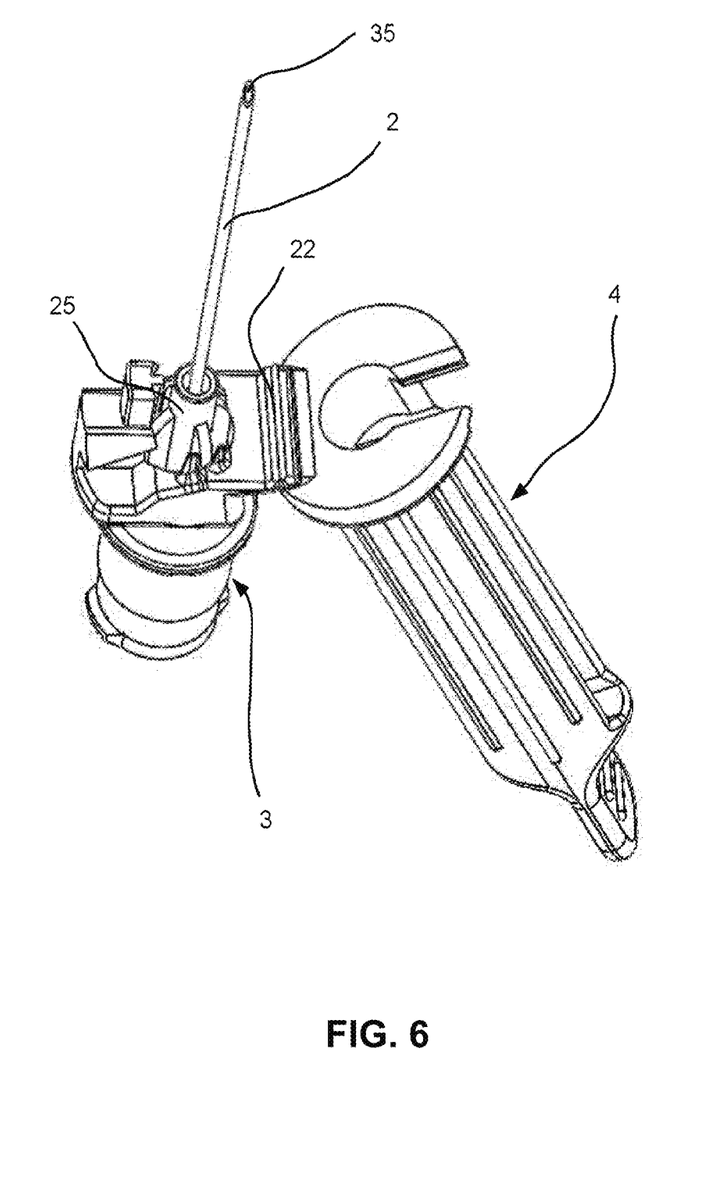
FIG. 6 illustrates a perspective view of the protective device according to FIG. 5.

When the cover 4 is in its operating position which is clearly evident from FIGS. 5 and 6, the needle tube 2 is released according to the preceding description so that the needle tube 2 is ready to be used for injection. In the illustrated embodiment, the base 3 is provided with an interlocking device 23 that is configured to cooperate with an interlocking partner 24 that is configured at the cover 4. Thus, the interlocking device 23 and the interlocking partner 24 can enter a positively form locking connection with one another so that the cover 4 is interlockable at the base when the cover 4 is in its operating position. This way an uncontrolled use of the cover 4, which would make a user of the syringe uncomfortable, is prevented when the needle tube 2 is used for injection.

After the needle tube 2 is used for injection, the cover 4 is pivoted from its operating position, back to the base 3 in a second pivot direction that is opposite to the first pivot direction until the cover 4 assumes protective position. It is essential for the protective position of the cover 4 that the cover 4 is pivoted far enough back in the second pivot direction so that the needle tube 2 enters into the interior 6 of the cover 4 again, and is thus protected against unintentional contact with a person. Since the needle tube 2 may have come in contact with a blood of a person, who has been injected with a medicine by the syringe, protection against a subsequent contact with the needle tube 2 is essential. Accordingly, it is necessary tube that cover 4 receives the needle tube 2 after being moved into the protective position so that an unintentional release of the needle tube 2 is rendered impossible thereafter.

In order to facilitate this, the cover 4 includes a retaining device 9, that includes a lobe 10, a stop 11, and two guide elements 12, 13. The retaining device 9 is visible in particular from the cross sections according to FIGS. 4 and 8. When the cover 4 is in its starting position, the needle tube 2 is arranged in a portion of the interior space 6 which is formed on a proximal side of the lobe 10 and thus outside of the safety area 7 of the interior space 6. In this condition, an exit of the needle tube 2 from the interior space 6 is not prevented, since the needle tube 2 has not been used for an injection yet. According to the preceding description the cover 4 is configured to be moved into an operating position where the needle tube 2 is released for use.

During pivoting of the cover 4 from the operating position back into the protective position, the retaining device 9 causes the needle tube 2 to be reliably retained in the interior 6 of the cover 4. Thus, the cover 4 is pivoted in the illustrated embodiment beyond the starting position in the second pivot direction so that longitudinal axes 5, 31 of the cover 4 and of the base 3 enclose an angle 32 relative to each other and therefore are not oriented parallel to one another. Thus, the angle 32 is approximately 20° in the illustrated embodiment. This movement of the cover 4 causes the needle tube 2 to not only enter the interior space 6 at the open side of the wall 30 of the cover 4 again but to enter the safety area 7 distal from the lobe 10. This is caused by displacing the lobe 10, upon its first contact with the needle tube 2 wherein the lobe 10 deforms due to its elastic properties. Starting from a predetermined position of the cover 4, the needle tube 2 snaps in place behind the lobe 10 which subsequently deforms back into its original shape. This condition is evident from FIG. 8.

A movement of the needle tube 2 from the safety area 7 is thus not possible any more. This is caused by the fact that the needle tube 2 itself even under a forced movement of the cover 4 in the first pivot direction, this means towards the operating position contacts a bottom side of the lobe 10, which deforms the lobe 10 elastically in a direction towards the open side of the wall 30. During this deformation, the lobe 10 contacts a lower contact surface 34 of the stop 11, at least with an end 16 of the lobe 10 that is oriented away from the wall 30, so that further deformation of the lobe 10 is prevented. This type of cooperation between lobe 10 and stop 11 is implemented in the illustrated embodiment, in that the lobe 10 and the stop 11 extend from opposite inner enveloping surfaces 14 of the wall 30 of the cover 4. The guide elements 12, 13 that are arranged on both sides of the stop 11, along the longitudinal axis 5 of the cover 4 and associated with the stop 11 prevent that the needle tube 2 can move in a space below the stop 11 after entering the safety area 7. Thus, a direct contact of the needle tube 2 with the contact surface 34 of the stop 11 is not possible. This prevents that the needle tube 2 can move from one side of the lobe 10 to an area above the end 16 of the lobe 10 and thus escape from the safety area 7.

According to the invention the lobe 10 extends with respect to the pivot plane 8 at a lobe angle 15 which is 40° in the illustrated embodiment. Furthermore, the lobe 10 is arranged relative to the needle tube 2 at the wall 30, so that a lobe base 26 is essentially at the same elevation level as the needle tube 2 when the cover 4 is in its starting position. Thus, the lobe base 26 and the needle tube 2 are in a common plane 27 when the cover 4 is in its starting position, wherein the common plane 27 is perpendicular to the pivot plane 8. This configuration helps to exclude a collision of the needle tube 2 with the lobe 10 when the protective device 1 is mounted at a needle carrier 25. This is clearly evident from FIG. 4, which clearly shows a corresponding offset between the needle tube 2 and the lobe 10.

In order to further simplify the entry of the needle tube 2 into the safety area 7 it is provided in the instant embodiment that an offset 18 measured perpendicular to the pivot plane 8, is provided between the end 16 of the lobe 10 that is oriented towards the lobe base 26 and an end 17 of the stop 11, that is oriented towards the lobe 10. Put differently a gap is provided between the lobe 10 and the stop 11, viewed in a direction orthogonal to the pivot plane 8. The same applies for the direction parallel to the pivot plane 8 where an offset 19 is provided between both ends 16, 17 of the lobe 10 and of the stop 11. The offset 18 measured orthogonal to the pivot plane 8 is 0.15 mm in the illustrated embodiment whereas the offset 19 is approximately 0.040 mm. This embodiment has proven particularly useful in order to minimize the collision risk between the lobe 10 and the needle tube 2, facilitate an easy transition of the needle tube 2 into the safety area 7 and furthermore cause a reliable stop of the lobe 10 at the contact surface 34 of the stop 11. With respect to the needle tube 2 entering the safety area 7, it has become evident that a force application required by the needle tube 2 upon the lobe 10 in order to deform the lobe 10 so that the needle tube 2 can enter the safety area 7 is particularly small. This has the advantage that the protective device 1 is also suitable for injecting substances that are injected with needle tubes 2 with a particularly small diameter. This applies in particular to insulin injections for which a needle tube 2 with a diameter of less than 0.2 mm is being used.

Particularly advantageously the protective device 1 includes additional guide elements 28 in addition to the guide elements 12, 13 wherein the additional guide elements 28 are arranged in the interior space 6 distributed along the longitudinal axis 5 of the cover 4. These guide elements 28 run like the guide elements 12, 13 from the inner enveloping surface 14 of the wall 30 of the cover 4. This is clearly evident from FIG. 1.

Figure 1:
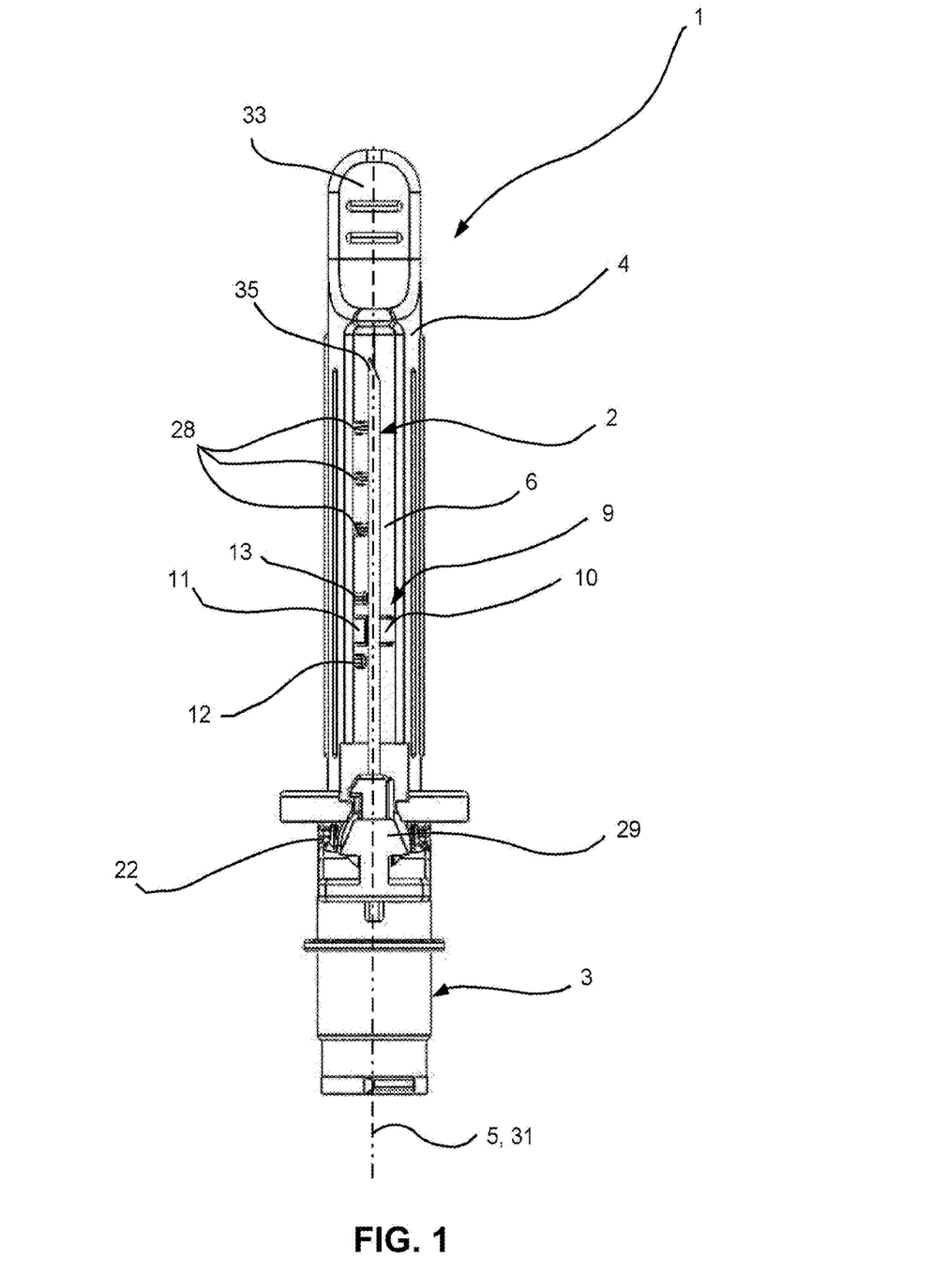
FIG. 1 illustrates a view of a protective device according to the invention with a cover in a starting position.
Figure 2:
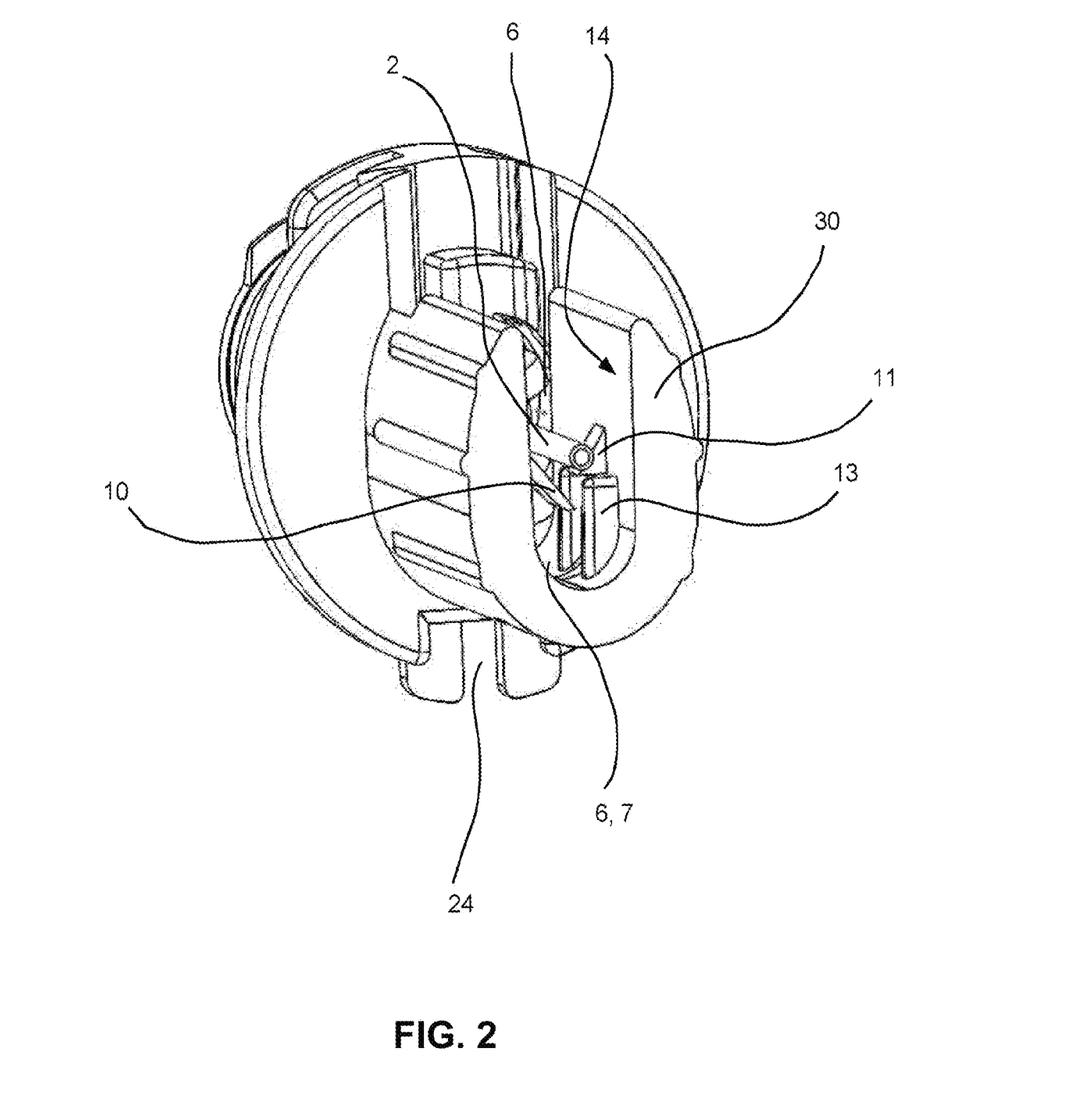
FIG. 2 illustrates a perspective cross sectional view of the protective device according to claim 1.
Figure 3:
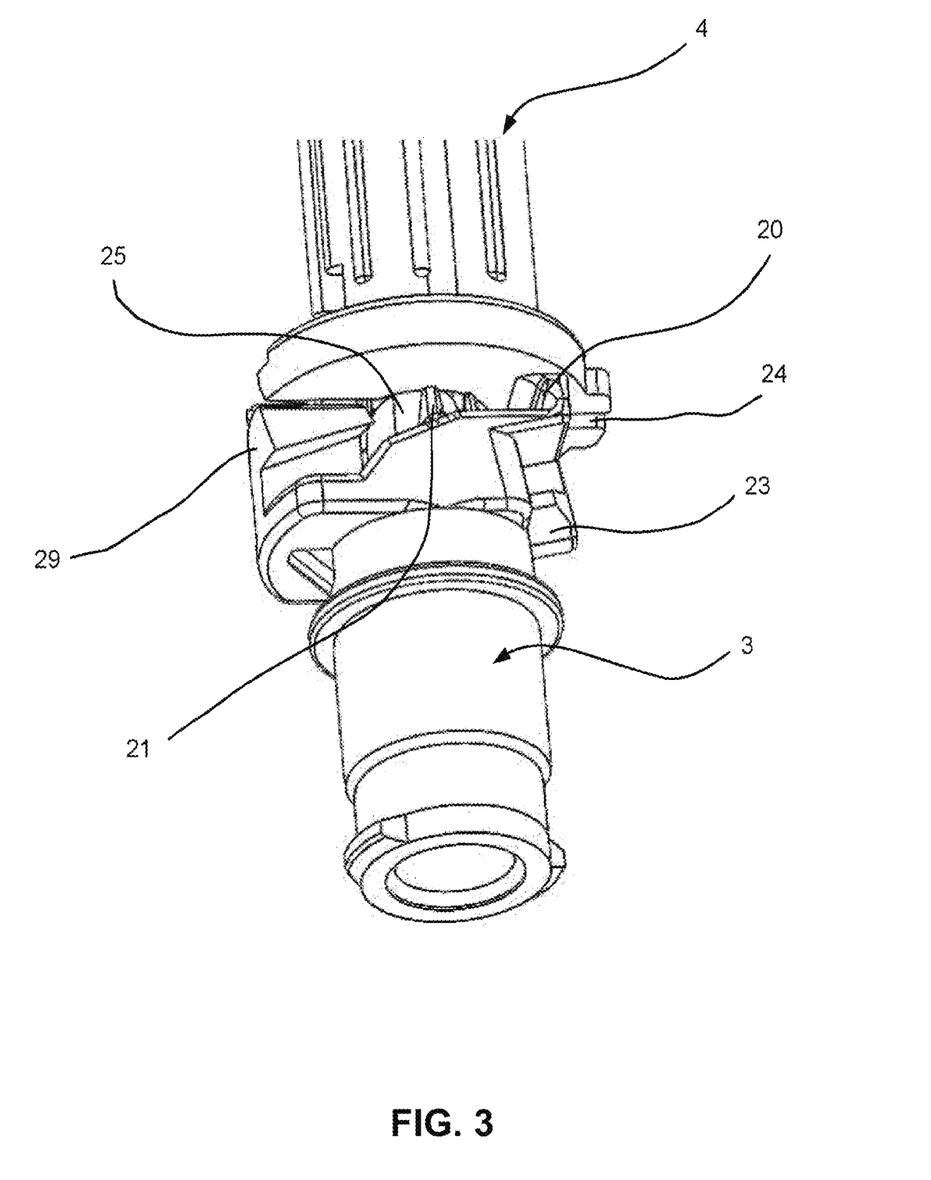
FIG. 3 illustrates a perspective view of a portion of the protective device according to FIG. 1.
Figure 4:
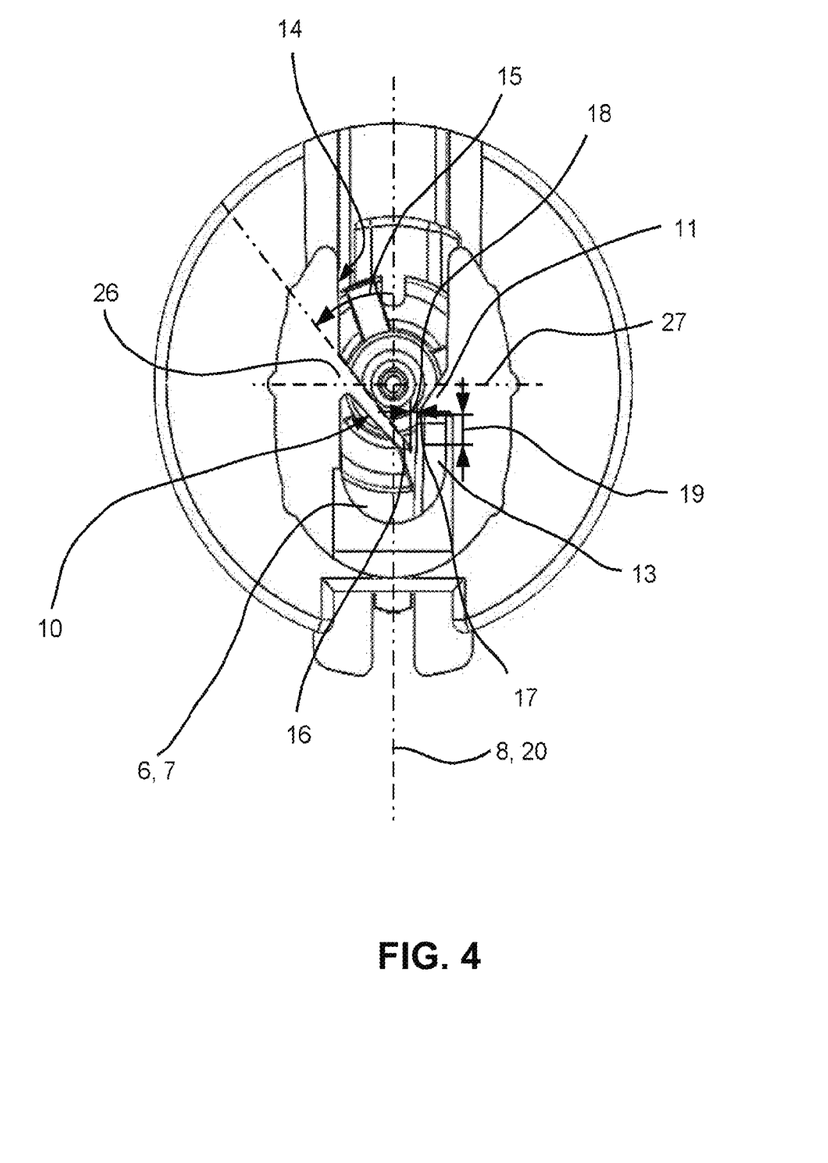
FIG. 4 illustrates a cross sectional view of the protective device according to FIG. 1.
Figure 7:
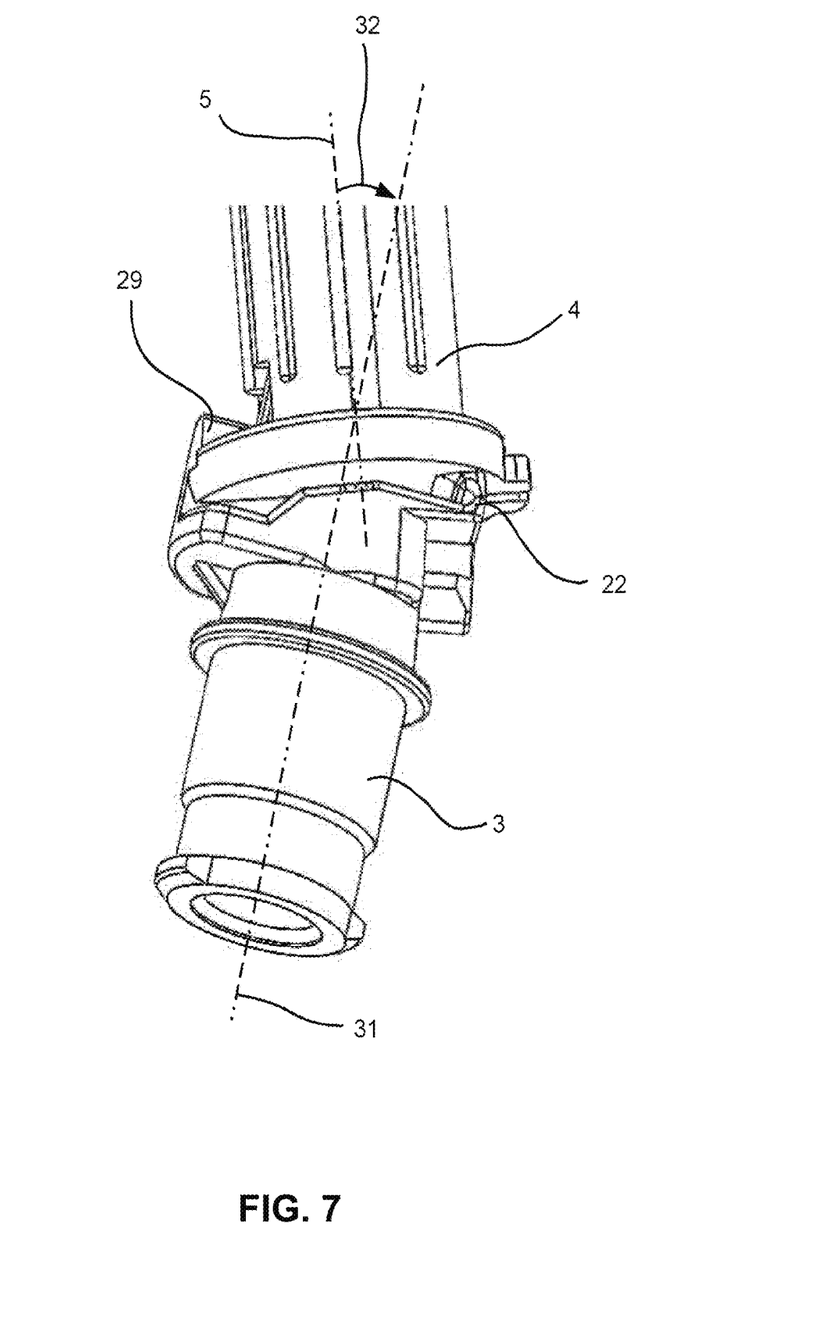
FIG. 7 illustrates a perspective view of a portion of the protective device according to FIG. 1 with the cover in a protective position.
Figure 8:
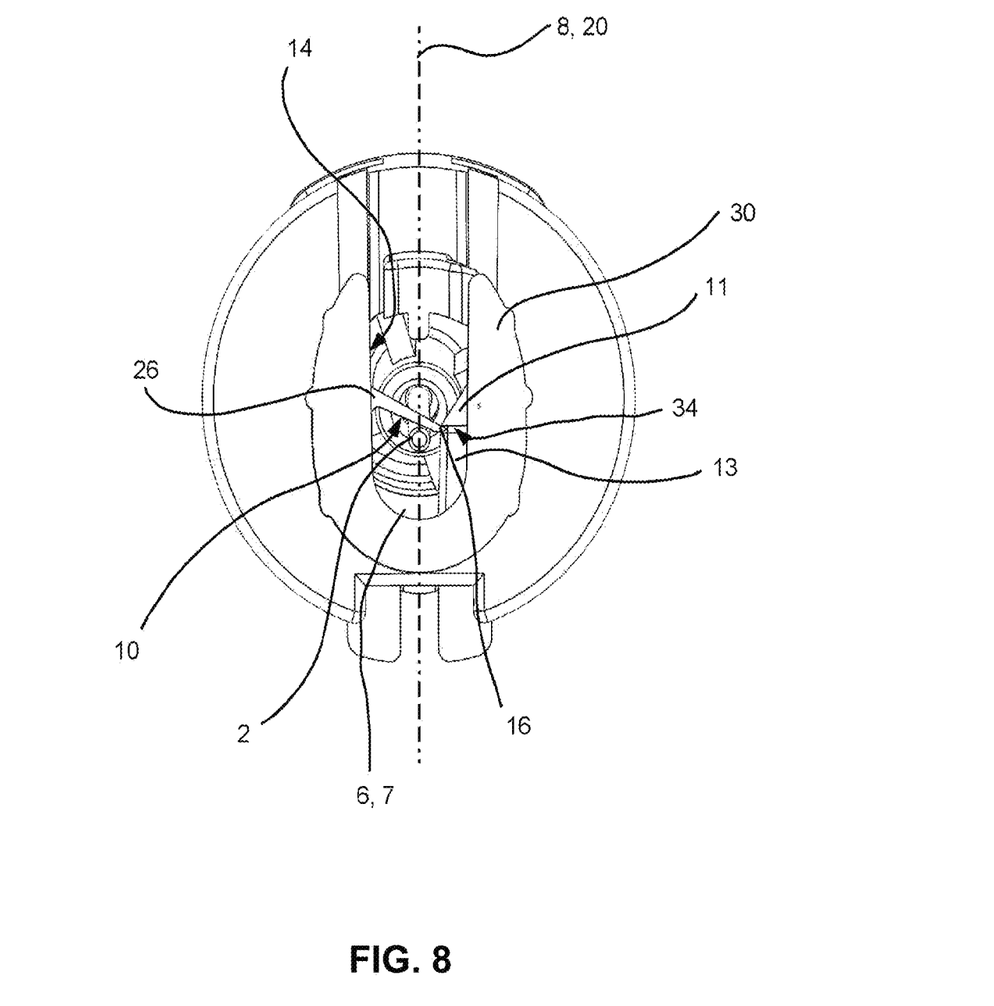
FIG. 8 illustrates a cross section through the cover of the protective device according to FIG. 7.

Furthermore, the base 3 includes a safety element 29 in the illustrated embodiment as evident from FIGS. 3 and 7. The safety element 29 locks the cover 4 at the base 2 by positive form locking when the cover 4 is moved into its protective position so that an unintentional pivoting of the cover 4 in a first pivot direction back into the operating position is prevented. This would require intentional force application upon the cover 4 in order to disengage the form locking with the safety element 29. Even in this case, the needle tube 2 would not be released since it is reliably retained in the safety area 7 of the interior 6 by the retaining device 9. Trials have shown that the needle tube 2 is bent and deformed in this case.

REFERENCE NUMERALS AND DESIGNATIONS 1 protective device
2 needle tube
3 base
4 cover
5 longitudinal axis
6 interior space
7 safety area
8 pivot plane
9 retaining device
10 lobe
11 stop
12 guide element
13 guide element
14 enveloping surface
15 lobe angle
16 end
17 end
18 offset
19 offset
20 vertical axis
21 rated fracture joint
22 foil hinge
23 interlocking device
24 interlocking partner
25 needle carrier
26 lobe base
27 plane
28 guide element
29 safety element
30 wall
31 longitudinal axis
32 angle
33 grip lobe
34 contact surface
35 needle tip

The invention claimed is:

1. A protective device for a needle tube of a syringe, the protective device comprising:
a base; and
a cover connected to the base,
wherein the base is configured to cooperate with a needle carrier by positive form locking wherein the needle carrier supports the needle tube,
wherein the cover is configured elongated along a longitudinal axis and defines an interior space in which the needle tube is storable so that a person is protected against an unintentional contact with the needle tube,
wherein the cover is pivotably supported at the base so that the cover is transferable relative to the base within a pivot plane from a starting position where the needle tube is stored in the interior space before being used for injection in a first pivot direction into an operating position where the needle tube is available for injection, and eventually transferrable in a second pivot direction opposite to the first pivot direction into a protective position where the needle tube is stored in the interior space again after being used for injection,
wherein the cover is open at one side in the pivot plane so that the needle tube is able to initially exit from the interior space for injection by performing the pivot movement of the cover in the first pivot direction and able to enter the interior space again by performing the pivot movement of the cover in the second pivot direction after being used for the injection,
wherein the cover includes a retaining device in the interior space wherein the retaining device is configured to interlock the needle tube by positive form locking during a transfer of the cover into the protective position so that an unintentional exit of the needle tube from the interior space is prevented after a completion of the transfer of the cover into the protective position,
wherein the retaining device includes a deformable lobe, a stop associated with the deformable lobe and at least one guide element,
wherein the deformable lobe is configured to be deformed by the needle tube during transfer of the cover into its protective position and displaced in a first displacement direction so that the needle tube is able to enter into a safety area arranged behind the deformable lobe in which the needle tube is interlocked behind the deformable lobe,
wherein the stop is configured at an inner enveloping surface of the cover opposite from the deformable lobe, so that the deformable lobe when deformed by the needle tube contacts a contact surface of the stop in a second displacement direction opposite to the first displacement direction so that an unintentional exit of the needle tube from the safety area is prevented,
wherein the guide element is associated with the stop and configured to guide the needle tube so that a presence of the needle tube below a stop surface of the stop is prevented after the needle tube enters the safety area, wherein the deformable lobe extends in undeformed condition from the inner enveloping surface of the cover into the interior space and defines a lobe angle of at least 35° with the pivot plane viewed in a cross section orthogonal to the longitudinal axis of the cover.

2. The protective device according to claim 1, wherein the lobe angle is at least 37.5°, or at least 40° in the undeformed condition of the deformable lobe (10).

3. The protective device according to claim 1,
wherein an offset measured in the direction orthogonal to the pivot plane is provided in a cross section of the cover orthogonal to the longitudinal axis of the cover between an end of the undeformed lobe oriented away from the inner enveloping surface of the cover and an end of the stop oriented towards the deformable lobe, wherein the offset is in a range between 0.05 mm and 0.25 mm, or between 0.10 mm and 0.20 mm.

4. The protective device according to claim 1, wherein a second offset is provided in a cross section of the cover orthogonal to the longitudinal axis of the cover between an end of the undeformed lobe oriented away from the inner enveloping surface of the cover and an end of the stop oriented towards the undeformed lobe, and
wherein the second offset is measured in a direction parallel to the pivot plane, and
wherein the second offset is in a range between 0.20 mm and 0.80 mm, or between 0.25 mm and 0.70 mm, or between 0.30 mm and 0.60 mm.

5. The protective device according to claim 1, wherein the at least one support element extends from the inner enveloping surface of the cover into the interior space.

6. The protective device according to claim 1,
wherein the at least one guide element includes a plurality of guide elements, and
wherein at least one guide element of the plurality of guide elements is arranged in front of the stop and at least one guide element of the plurality of guide elements is arranged behind the stop viewed in the longitudinal direction of the cover.

7. The protective device according to claim 1,
wherein the cover is configured U-shaped in a cross section orthogonal to its longitudinal axis, and
wherein a vertical axis of the cross section is oriented parallel to the pivot plane of the cover.

8. The protective device according to claim 1,
wherein the base and the cover are connected with one another by a rated fracture joint when the cover is in the starting position, and
wherein the rated fracture joint is breakable by a hand force so that the cover is pivotable into the operating position after breaking the rated fracture joint.

9. The protective device according to claim 1, wherein the cover and the base are connected with one another by a film hinge.

10. The protective device according to claim 1,
wherein the cover and the base are arranged coaxial in the starting position, and
wherein the cover is pivoted beyond the starting position in the second pivot direction when the cover is in the protective position.

11. The protective device according to claim 1, further comprising:
an interlocking device configured at the base,
wherein the interlocking device is configured to engage an interlocking partner of the cover by positive form locking so that the cover is interlockable in the protective position.

12. A set, comprising:
the protective device according to claim 1; and
the needle carrier with the needle tube supported therein,
wherein the base of the protective device is connected with the needle carrier by positive form locking, so that the needle tube is oriented parallel to the longitudinal axis of the cover when the cover is in the starting position.

13. The set according to claim 12, wherein a lobe base of the deformable lobe that connects the deformable lobe at the inner enveloping surface of the cover is arranged in a common plane with the needle tube when the cover is in its starting position viewed in a cross section of the cover orthogonal to the longitudinal axis of the cover, wherein the common plane is perpendicular to the pivot plane.

* * * * *